United States Patent [19]

Shinozaki et al.

[11] 3,983,008
[45] Sept. 28, 1976

[54] METHOD OF EXTRACTING USEFUL COMPONENTS FROM MICROBIAL CELLS

[75] Inventors: Tatsuo Shinozaki; Nobuyuki Kikkawa; Fumiaki Fujitani; Kenjiro Tanaka, all of Sodegaura, Japan

[73] Assignee: Idemitsu Kosan Co., Ltd., Tokyo, Japan

[22] Filed: May 20, 1975

[21] Appl. No.: 579,228

[30] Foreign Application Priority Data
May 27, 1974 Japan.................................. 49-58860

[52] U.S. Cl.............................. 195/104; 195/66 R; 260/112 R; 260/412.8
[51] Int. Cl.$^2$........................................... C12B 1/00
[58] Field of Search............. 195/1.28 R, 104, 66 R; 260/112 R, 412.8; 241/2, 1, 301

[56] References Cited
UNITED STATES PATENTS

| | | | |
|---|---|---|---|
| 2,928,614 | 3/1960 | Emanuel et al.......................... | 241/1 |
| 3,375,174 | 3/1968 | Crabbe et al........................ | 195/104 |

*Primary Examiner*—R. B. Penland
*Attorney, Agent, or Firm*—Flynn & Frishauf

[57] ABSTRACT

Method of extracting a useful component from microbial cells by disrupting microbial cells. Microbial cells are disrupted in one or more stages in a high-pressure multi-stage homogenizer and said disrupted cells are contacted with solvent in one or more remaining stages of the homogenizer to extract a useful component.

9 Claims, 1 Drawing Figure

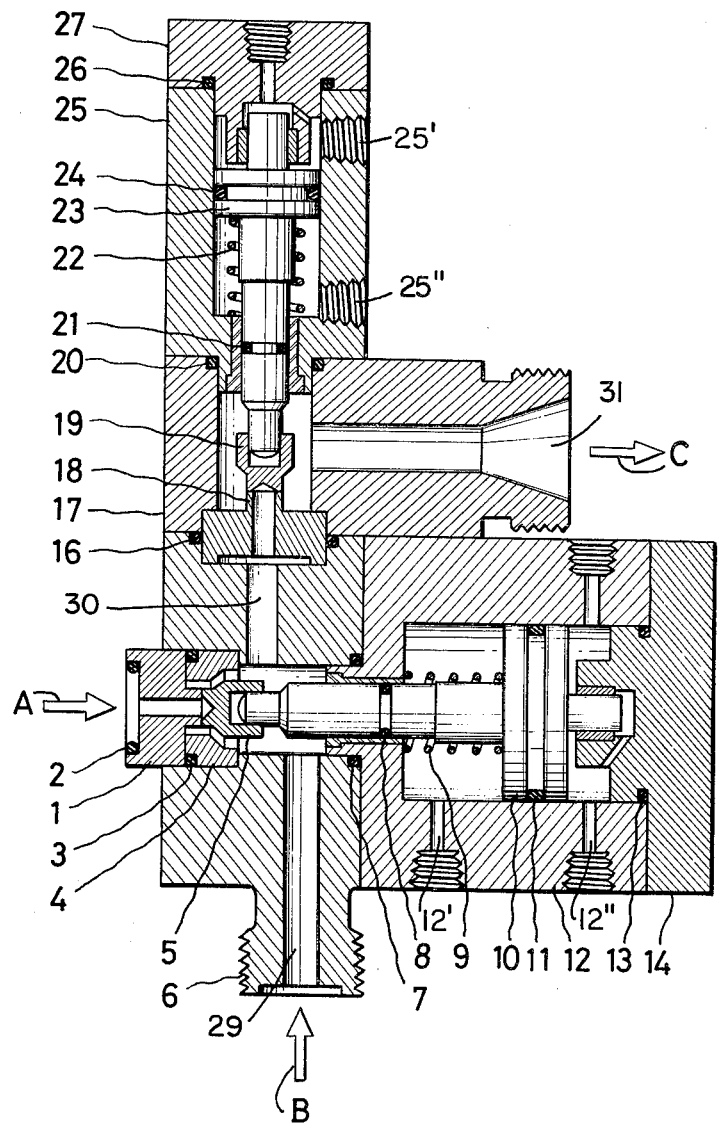

METHOD OF EXTRACTING USEFUL COMPONENTS FROM MICROBIAL CELLS

BACKGROUND OF THE INVENTION

A. Field of the Invention

The present invention relates to a method of extracting a useful component from microbial cells. More specifically, microbial cells are disrupted during one or more stages of high-pressure multi-stage homogenization, and said disrupted cells are contacted with solvent during one or more remaining stages of the homogenization to extract a useful component.

B. Description of the Prior Art

As a method of extracting useful components from microbial cells, it has been known that extraction of useful components can be carried out by treating a mixture of microbial cells and an extracting solvent in a homogenizer to disrupt a cell wall and a cell membrane and extract useful components from the disrupted cells. It has also been known to disrupt microbial cells in the homogenizer and then extract useful components from the disrupted cells with extracting solvent in an agitation vessel.

However, in the former method efficiency of disruption of the cell wall and the cell membrane is often lowered by the presence of solvent. The latter method is disadvantageous for practical applications, since it requires a large agitation vessel, resulting in high operating costs.

SUMMARY OF THE INVENTION

It is an object of this invention to provide a method of extracting useful components from microbial cells.

The method of the present invention is carried out by the use of a high-pressure multi-stage homogenizer.

According to the present invention, various useful components, for example proteins, nucleic acids, amino acids, vitamins, enzymes and antibiotics, can be extracted with high efficiency.

BRIEF DESCRIPTION OF THE DRAWING

The single FIGURE is a cross-sectional view of a high-pressure two-stage homogenizer for carrying out the present invention.

DETAILED DESCRIPTION

The method of the present invention comprises two steps, that is, a disruption step and an extraction step.

Various microorganisms can be employed in the method of the present invention. Examples of these microorganisms are yeasts belonging to genus Pichia, Hansenula, Debaryomyces, Cryptococcus, Torulopsis, Candida, Rhodotorula, Trichosporon, Saccharomyces, etc.; bacteria belonging to genus Micrococcus, Pseudomonas, Bacillus, Mycobacterium, Streptococcus, Acetobacter, Brevibacterium, etc.; fungi belonging to genus Aspergillus, Penicillium, Rhizopus, Mucor, etc.; actinomyces belonging to Streptomyces, etc.; and algae belonging to genus Chlorella, Senedesumus, Spirulina, etc.

These microorganisms are fed to a high-pressure multi-stage homogenizer in a fluid state, such as an aqueous suspension at a cellular concentration of 1–25% (w/v).

Preferable examples of high-pressure multi-stage homogenizers applicable for the present invention are two to four-stage homogenizers. A two-stage homogenizer is shown in the single Figure and will be described hereinbelow.

In a multi-stage homogenizer, the first stage and, if necessary, succeeding one or more intermediate stages, except a last stage, are utilized to perform mainly disruption of microbial cells. Remaining stages, that is, a stage or stages following the last disruption stage or only the final stage, are used for contacting the disrupted cells with an extracting solvent.

As an extracting solvent, any solvent conventionally used with microbial cells can be successfully used in the method of the present invention.

When a solvent is used for extracting amino acids, proteins, vitamins, nucleic acids, etc., from microbial cells, water; an aqueous solution of a base such as NaOH, KOH, $Ca(OH)_2$ and $NH_4OH$; an aqueous solution of an acid such as HCl, $H_2SO_4$, $H_3PO_4$, acetic acid and citric acid; an aqueous solution of a salt such as NaCl, $NaHCO_3$, $Na_2CO_3$, $CaCl_2$ and KCl; and various buffer solutions such as Clark-Lub's, Srensen's, Kolthoff's, Michaelis's, AtkinsPantin's, Gomori's buffer solution and the like, can be used. Examples of a solvent for extracting lipids and vitamins are organic solvents such as methanol, ethanol, isopropanol, n-hexane, ether, acetone, chloroform, benzene and toluene.

Furthermore, a surface active agent can be added to the above-mentioned solvents if required. Examples of such surface active agent are: non-ionic agents such as polyoxyethylene sorbitan acyl esters and polyoxyethylene acyl esters; cationic agents such as alkylpyridinium halides, benzalkonium halides and alkyl ammonium halides; and anionic agents such as acyl sulfones and sodium alkyl benzene sulfonates.

The extracting solvent is employed in an amount of from 0.05 to 50 parts (volume) in case of an organic solvent, and from 0.001 to 5 parts (volume) in case of other solvents, based upon one part of an aqueous suspension of microbial cells. Supply of solvent can be made at any desired positions between the outlet of the first stage of the homogenizer and the inlet of the final stage, and can be introduced through only one position or through a plurality of positions by dividing the solvent into a plurality of portions.

Referring to the single FIGURE, a typical two-stage homogenizer includes a first homogenizer stage comprised of first homogenizer valve body 6 housing first homogenizer valve 5 which cooperates with first homogenizer breaker ring 4. The input medium to the first homogenizer valve is fed in the direction of arrow A through an opening in first valve seat 1, an O-ring 2 being provided for sealing. An O-ring 3 is provided for sealing the homogenizer valve within the first valve body 6. First homogenizer valve rod 10 is cooperatively coupled with the first homogenizer valve 5 to adjust same. The homogenizer valve 10 is slideably mounted within first oil pressure cylinder 12 which receives oil pressure through channels 12' and 12'' for adjusting the position thereof. Spring 9 biases the valve rod 10 toward the right as seen in the FIGURE. O-ring 7 is provided to seal the junction between the valve body 6 and the oil pressure cylinder 12. Additional O-rings 8 and 11 are provided for sealing purposes within the oil pressure cylinder 12. Cover 14 is provided for the oil pressure cylinder 12 and is sealed thereto through O-ring 13. Channel 29 is provided in valve body 6 to supply aqueous solution to mix with the output of the first homogenizer stage.

The output of the first homogenizer stage communicates with a second homogenizer stage through channel 30 formed in the first homogenizer valve body 6. The channel 30 leads to second homogenizing valve seat 18 which cooperates with second homogenizer valve 19, valve seat 18 and valve 19 being mounted to second homogenizer valve body 17. O-ring 16 seals the junction between the first and second homogenizer valve bodies 6, 17. Second oil pressure cylinder 25 is mounted to the second valve body 17 and is sealed thereto via O-ring 20. Second pressure cylinder 25 houses second homogenizer valve rod 23, which is similar to but smaller than valve rod 10 of the first homogenizer valve. Second spring 22 is provided to bias the valve rod 23 in the upward direction as viewed in the Figure. Oil pressure is communicated with second oil pressure cylinder 25 via channels 25' and 25''. Oil pressure cover 27 is sealed to the second oil pressure cylinder 25 via O-ring 26, and further O-rings 21 and 24 are provided for appropriately sealing the second valve rod 23 to the second oil pressure cylinder 25. Outlet port 31 leads out from the second homogenizer as indicated by the arrow C.

The operation of the above-described homogenizer system illustrated in the FIGURE is self-explanatory, and further description is not given herein for the sake of brevity.

On performing the method of the present invention, the two steps described above, that is, the disruption step and the extraction step, are carried out under high pressure. The pressure is expressed herein by the term "pressure difference." Pressure difference means the difference between a pressure (higher pressure) in the inlet stage and a pressure (lower pressure) out of the same stage. The pressure difference of a stage performing mainly disruption of microbial cells is from 100 to 1500 kg/cm$^2$, and the pressure difference of a stage for extracting useful components is set at from 0.1 to 300 kg/cm$^2$. For example, in case of extraction of protein from yeast cells, the pressure difference of the stage performing mainly disruption of microbial cells is set above 100 kg/cm$^2$. After a sufficient disruption of the cells, an alkaline solution such as sodium hydroxide solution is introduced as an extracting solvent into a path between the first stage and the second stage, and then extraction of protein is performed.

Feeding of a suspension of microbial cells and an extracting solvent to the homogenizer can be performed at a temperature of from 0° to 100°C.

According to the method of the present invention, high efficiency of disruption of microbial cells can easily be obtained. A large agitation vessel used in the prior conventional method referred to above is not required. Accordingly, the extraction process can be simplified and operating costs are lowered.

As described in the above, the practical significance of the present invention is great in the fields of fermentation industry, food industry and pharmaceutical industry utilizing microbial cells.

The method is illustrated by the following typical examples.

EXAMPLE 1

Protein was extracted from yeast (*Saccharomyces cerevisiae*) using a two-stage homogenizer (Sanwa Machinery Co., Type H50). A typical homogenizer is shown in the single FIGURE.

An aqueous suspension of yeast (cell concentration of 10% w/v) was introduced to a first stage of the homogenizer (arrow A in the Figure) at a rate of 240 l/hr with aid of a high-pressure pump (not shown), and an aqueous solution of 40% of NaOH was introduced between the first stage and the second stage (through channel 29 - arrow B in the FIGURE) of the homogenizer at a rate of 3 l/hr using another feeding pump (not shown). The pressure difference in the first stage and in the second stage was set at 797 kg/cm$^2$ and 3 kg/cm$^2$, respectively.

A treated mixture emerged from the outlet port 31 indicated by the arrow C in the FIGURE at steady state and was centrifuged for 20 min. at 10,000 × g. Amounts of protein in the supernatant fluid were measured. The extraction yield was found to be 79%. The extraction yield was expressed as the ratio of total nitrogen in the supernatant fluid to total nitrogen of the yeast cells. Determination of nitrogen was conducted by the micro Kjeldahl method.

COMPARATIVE EXAMPLE 1

An aqueous suspension of yeast (cell concentration of 10% w/v) was introduced to a two-stage homogenizer at a rate of 240 l/hr. The pressure difference in the first stage and in the second stage was set at 797 kg/cm$^2$ and 3 kg/cm$^2$, respectively.

A treated solution discharged from the outlet 31 indicated by the arrow C in the FIGURE at steady state was transferred to an agitation vessel and then a 40% NaOH solution was added to it in the same ratio as used in Example 1 in order to extract protein for a prescribed time.

The extraction yield (determined by the same method as described in Example 1) is shown in Table 1.

Table 1

| Extraction Time (min.) | 5 | 10 | 20 | 30 | 60 |
|---|---|---|---|---|---|
| Extraction Yield (%) | 70 | 73 | 74 | 78 | 79 |

COMPARATIVE EXAMPLE 2

A solution of 40% NaOH was added to an aqueous suspension of yeast (cell concentration of 10% w/v) in the same ratio as shown in Example 1 and was mixed together for a prescribed time. Subsequently, the mixture was fed to a two-stage homogenizer at a rate of 240 l/hr. The pressure difference in the first stage was set at 797 kg/cm$^2$ and that of the second stage was set at 3 kg/cm$^2$.

The extraction yield (determined by the same method as shown in Example 1) is described in Table 2.

Table 2

| Soaking Time (min.) | 2 | 3 | 5 | 10 | 20 |
|---|---|---|---|---|---|
| Extraction Yield (%) | 72 | 70 | 68 | 62 | 54 |

EXAMPLE 2

An enzyme (glutamate dehydrogenase) was extracted from bacterium (glutamic acid-producing bacterium, Brevibacterium sp.) using the same two-stage homogenizer as used in Example 1.

An aqueous suspension of the bacteria at a concentration of 9.3% w/v was introduced to a first stage of the homogenizer at a rate of 240 l/hr. An ice-cooled extracting solvent comprising 2.5 parts (vol.) of 0.2 M Tris-buffer (pH 7.6), 1.2 parts (vol.) of 0.1 M mercaptoethanol and 0.2 parts (vol.) of 0.1 M $MgCl_2.6H_2O$ was introduced into the homogenizer between the first and second stages at a rate of 96 l/hr. The pressure difference in the first stage and in the second stage was set at 490 $kg/cm^2$ and 10 $kg/cm^2$, respectively.

A treated solution thus obtained at steady state was immediately centrifuged at 16,000 × g for 20 minutes and an enzyme solution was obtained. This enzyme solution exhibited an activity of 1420 units/ml, where the activity was measured by an increase in optical density at 340 m$\mu$ of the reaction mixture after incubating at 30°C. The reaction mixture contains 200 $\mu$ mol of Tris-buffer, 20 $\mu$ mol of $MgCl_2.6H_2O$, 100 $\mu$ mol of glutamic acid, 0.3 $\mu$ mol of Na $DP^+$ (Nicotinamide diphosphate$^+$) and aliquots of the enzyme solution, in a total of 3 ml (pH 8.8). Change in the optical density of 0.001/min. was defined as 1 unit.

EXAMPLE 3

Lipids were extracted from yeast (*Candida utilis*) using the same two-stage homogenizer employed in Example 1.

An aqueous suspension of yeast at a concentration of 10.8% w/v was introduced to the first stage of the homogenizer at a rate of 240 l/hr, and n-hexane was introduced into the homogenizer between the first and the second stages at a rate of 100 l/hr. The pressure difference in the first and second stages was set at 800 $kg/cm^2$ and 50 $kg/cm^2$, respectively.

A treated solution thus obtained at steady state (90 ml) was immediately centrifuged for 20 min. at 1,500 x g, resulting in separation into 6 layers. The upper three layers were rich in hexane and these layers were concentrated with a rotary evaporator to dryness. Subsequently, extraction and purification were performed with a mixture of methanol and chloroform according to the Folch method, and thus 0.271 g. of lipids were obtained. This data indicates that 5.6 weight percent of lipids was extracted from the cells; therefore, the extraction yield is calculated as 51.4%.

What is claimed is:

1. A method of extracting a component from microbial cells containing the same, which comprises disrupting microbial cells in a first stage in a high-pressure multi-stage homogenizer in the absence of a solvent for extracting said component from the cells, and contacting said disrupted cells with a solvent in a directly succeeding stage of said homogenizer to extract said component from the cells.

2. The method according to claim 1, wherein said homogenizer is a high-pressure, two-stage homogenizer wherein the disrupting step is carried out in the first stage and the extracting step is carried out in the second stage.

3. The method according to claim 1, wherein said disrupting step is carried out at a pressure difference of from 100 to 1500 $kg/cm^2$ and the extracting step is carried out at a pressure difference of from 0.1 to 300 $kg/cm^2$.

4. The method according to claim 2, wherein said disrupting step is carried out at a pressure difference of from 100 to 1500 $kg/cm^2$, and the extracting step is carried out at a pressure difference of from 0.1 to 300 $kg/cm^2$.

5. The method according to claim 1, wherein microbial cells are fed to said homogenizer as an aqueous suspension having a cell concentration of from 1 to 25% w/v.

6. The method according to claim 2, wherein microbial cells are fed to said homogenizer as an aqueous suspension having a cell concentration of 1 to 25% w/v.

7. The method according to claim 1, wherein said microbial cells are yeast cells or bacterium cells.

8. The method according to claim 2, wherein said microbial cells are yeast cells or bacterium cells.

9. The method of claim 1, wherein said first stage comprises a plurality of disruption stages.

* * * * *

UNITED STATES PATENT OFFICE
CERTIFICATE OF CORRECTION

PATENT NO. : 3,983,008
DATED : September 28, 1976
INVENTOR(S) : TATSUO SHINOZAKI et al It is certified that error appears in the above-identified patent and that said Letters Patent are hereby corrected as shown below:

Column 5, line 17: replace "Na DP$^+$" with --- NADP$^+$ ---.

Signed and Sealed this second Day of August 1977

[SEAL]

Attest:

RUTH C. MASON
Attesting Officer

C. MARSHALL DANN
Commissioner of Patents and Trademarks